(12) United States Patent
Babcock et al.

(10) Patent No.: US 11,174,447 B2
(45) Date of Patent: Nov. 16, 2021

(54) LUBRICIOUS COATINGS WITH SURFACE SALT GROUPS

(71) Applicant: Surmodics, Inc., Eden Prairie, MN (US)

(72) Inventors: David E. Babcock, Brooklyn Park, MN (US); Joram Slager, St. Louis Park, MN (US); Robert W. Hergenrother, Vestavia, AL (US)

(73) Assignee: Surmodics, Inc., Eden Prairie, MN (US)

( * ) Notice: Subject to any disclaimer, the term of this patent is extended or adjusted under 35 U.S.C. 154(b) by 107 days.

(21) Appl. No.: 16/505,145

(22) Filed: Jul. 8, 2019

(65) Prior Publication Data

US 2019/0330551 A1 Oct. 31, 2019

Related U.S. Application Data

(63) Continuation of application No. 15/375,442, filed on Dec. 12, 2016, now Pat. No. 10,342,898.

(60) Provisional application No. 62/272,440, filed on Dec. 29, 2015.

(51) Int. Cl.
| | | |
|---|---|---|
| *B32B 27/30* | (2006.01) | |
| *A61L 27/34* | (2006.01) | |
| *A61L 27/28* | (2006.01) | |
| *A61L 31/10* | (2006.01) | |
| *A61L 31/08* | (2006.01) | |
| *A61L 29/08* | (2006.01) | |
| *C10M 107/26* | (2006.01) | |
| *C10M 107/46* | (2006.01) | |
| *C10M 107/42* | (2006.01) | |
| *A61M 25/10* | (2013.01) | |
| *B32B 27/00* | (2006.01) | |
| *C10N 40/00* | (2006.01) | |
| *C10N 50/08* | (2006.01) | |

(52) U.S. Cl.
CPC ........... *C10M 107/26* (2013.01); *A61L 27/34* (2013.01); *A61M 25/104* (2013.01); *B32B 27/00* (2013.01); *B32B 27/30* (2013.01); *B32B 27/308* (2013.01); *C10M 107/42* (2013.01); *C10M 107/46* (2013.01); *C10M 2209/0606* (2013.01); *C10M 2217/0285* (2013.01); *C10M 2221/025* (2013.01); *C10N 2040/50* (2020.05); *C10N 2050/08* (2013.01)

(58) Field of Classification Search
None
See application file for complete search history.

(56) References Cited

U.S. PATENT DOCUMENTS

| | | |
|---|---|---|
| 4,195,637 A | 4/1980 | Gruntzig et al. |
| 4,876,126 A | 10/1989 | Tanabe et al. |
| 4,973,493 A | 11/1990 | Guire |
| 4,979,959 A | 12/1990 | Guire |
| 4,990,357 A | 2/1991 | Karakelle et al. |
| 5,001,009 A | 3/1991 | Whitbourne et al. |
| 5,002,582 A | 3/1991 | Guire et al. |
| 5,039,485 A | 8/1991 | Conviser et al. |
| 5,041,089 A | 8/1991 | Mueller et al. |
| 5,087,246 A | 2/1992 | Smith |
| 5,091,205 A * | 2/1992 | Fan .............. C08G 18/625 427/2.28 |
| 5,135,516 A * | 8/1992 | Sahatjian ............ A61L 33/0023 427/2.24 |
| 5,263,992 A | 11/1993 | Guire |
| 5,318,587 A | 6/1994 | Davey |
| 5,382,234 A | 1/1995 | Cornelius et al. |
| 5,414,075 A | 5/1995 | Swan et al. |
| 5,512,329 A | 4/1996 | Guire et al. |
| 5,554,120 A | 9/1996 | Chen et al. |
| 5,571,089 A | 11/1996 | Crocker |
| 5,637,460 A | 6/1997 | Swan et al. |
| 5,662,960 A | 9/1997 | Hostettler et al. |
| 5,670,558 A | 9/1997 | Onishi et al. |
| 5,714,360 A | 2/1998 | Swan et al. |
| 5,731,087 A | 3/1998 | Fan et al. |
| 5,776,101 A | 7/1998 | Goy |

(Continued)

FOREIGN PATENT DOCUMENTS

| | | |
|---|---|---|
| CN | 104185661 | 8/2016 |
| CN | 108697825 | 10/2018 |

(Continued)

OTHER PUBLICATIONS

Allcock, H R. et al., "Molecular Weight," Contemporary Polymer Chemistry, (1990), p. 271.
File History for U.S. Appl. No. 15/375,442 downloaded Jul. 30, 2019 (1541 pages).
File History for European Patent Application No. downloaded Jul. 30, 2019 (321 pages).
File History for U.S. Patent Application No. downloaded Jul. 30, 2019 (1345 pages).
File History for U.S. Patent Application No. downloaded Jul. 30, 2019 (1159 pages).

(Continued)

*Primary Examiner* — Sheeba Ahmed
(74) *Attorney, Agent, or Firm* — Pauly, DeVries Smith & Deffner LLC

(57) ABSTRACT

Embodiments herein include coated medical devices and coatings with salt groups. In an embodiment, a coated medical device is included, the coated medical device including a substrate and a polymeric layer disposed over the substrate. The polymeric layer includes a polymer and has an exterior surface. The coated medical device further includes a plurality of salt groups bonded to the polymer of the polymeric layer and disposed on the exterior surface of the polymeric layer. The salt groups can be the reaction product of a reactive group with an acid or base. In an embodiment, a method of making a medical device is included. Other embodiments are also included herein.

18 Claims, 4 Drawing Sheets

(56) References Cited

U.S. PATENT DOCUMENTS

| | | | |
|---|---|---|---|
| 5,807,331 A | 9/1998 | Heijer et al. |
| 5,849,846 A | 12/1998 | Chen et al. |
| 5,858,653 A | 1/1999 | Duran et al. |
| 5,882,336 A | 3/1999 | Janacek |
| 5,891,109 A | 4/1999 | Inoue et al. |
| 6,066,118 A | 5/2000 | Inoue et al. |
| 6,077,698 A | 6/2000 | Swan et al. |
| 6,156,345 A | 12/2000 | Chudzik et al. |
| 6,176,849 B1 | 1/2001 | Yang et al. |
| 6,278,018 B1 | 8/2001 | Swan |
| 6,394,995 B1 | 5/2002 | Solar et al. |
| 6,517,515 B1 | 2/2003 | Eidenschink |
| 6,603,040 B1 | 8/2003 | Swan |
| 6,623,504 B2 | 9/2003 | Vrba et al. |
| 6,896,842 B1 | 5/2005 | Hamilton et al. |
| 6,924,390 B2 | 8/2005 | Swan |
| 7,056,533 B2 | 6/2006 | Chudzik et al. |
| 7,138,541 B2 | 11/2006 | Swan |
| 7,163,523 B2 | 1/2007 | Devens, Jr. et al. |
| 7,192,484 B2 | 3/2007 | Chappa et al. |
| 7,348,055 B2 | 3/2008 | Chappa et al. |
| 7,550,444 B2 | 6/2009 | Stucke et al. |
| 7,691,476 B2 | 4/2010 | Finley et al. |
| 7,772,393 B2 | 8/2010 | Guire et al. |
| 8,889,760 B2 | 11/2014 | Kurdyumov et al. |
| 8,927,000 B2 | 1/2015 | Chappa et al. |
| 9,340,876 B2 | 5/2016 | Kim |
| 9,375,517 B2 | 6/2016 | Babcock |
| 9,737,639 B2 | 8/2017 | Babcock |
| 10,124,088 B2 | 11/2018 | Chappa et al. |
| 10,342,898 B2 * | 7/2019 | Babcock | B05D 3/007 |
| 10,905,802 B2 | 2/2021 | Babcock et al. |
| 2002/0002353 A1 | 1/2002 | Michal et al. |
| 2003/0165613 A1 | 9/2003 | Chappa et al. |
| 2005/0163853 A1 | 7/2005 | Szente et al. |
| 2008/0213334 A1 | 9/2008 | Lockwood et al. |
| 2009/0263449 A1 | 10/2009 | Mcgonigle et al. |
| 2010/0198168 A1 | 8/2010 | Rooijmans |
| 2010/0272774 A1 | 10/2010 | Chappa |
| 2010/0274012 A1 | 10/2010 | Guire et al. |
| 2011/0046255 A1 | 2/2011 | Rooijmans |
| 2011/0059874 A1 | 3/2011 | Rooijmans et al. |
| 2011/0144373 A1 | 6/2011 | Swan et al. |
| 2011/0245367 A1 | 10/2011 | Kurdyumov et al. |
| 2012/0046384 A2 | 2/2012 | Kurdyumov et al. |
| 2012/0149934 A1 | 6/2012 | Kurdyumov |
| 2012/0253296 A1 | 10/2012 | Amano et al. |
| 2013/0143056 A1 | 6/2013 | Swan et al. |
| 2013/0197433 A1 | 8/2013 | Babcock |
| 2013/0337147 A1 | 12/2013 | Chappa et al. |
| 2014/0004158 A1 | 1/2014 | Mcgonigle |
| 2014/0162083 A1 | 6/2014 | Kurdyumov et al. |
| 2014/0193474 A1 * | 7/2014 | Babcock | A61L 29/14 424/422 |
| 2015/0140107 A1 | 5/2015 | Slager et al. |
| 2016/0089480 A1 | 3/2016 | Chappa et al. |
| 2016/0271300 A1 | 9/2016 | Babcock |
| 2017/0182224 A1 | 6/2017 | Babcock et al. |
| 2017/0304506 A1 | 10/2017 | Babcock |

FOREIGN PATENT DOCUMENTS

| | | |
|---|---|---|
| CR | 2014-0349 | 11/2014 |
| EP | 0747071 | 12/1996 |
| EP | 0829264 | 3/1998 |
| EP | 2505215 | 10/2012 |
| EP | 2692365 | 2/2014 |
| EP | 2804915 | 3/2016 |
| EP | 3012301 | 4/2016 |
| EP | 3200844 | 8/2017 |
| EP | 3397296 | 11/2018 |
| EP | 3200844 | 8/2020 |
| IN | 6113/CHENP/2014 A | 7/2016 |
| JP | S60259269 | 12/1985 |
| JP | 09276392 | 10/1997 |
| JP | 11114052 | 4/1999 |
| JP | 2001017536 | 1/2001 |
| JP | 2008522670 | 7/2008 |
| JP | 2011509944 | 3/2011 |
| JP | 2013523751 | 6/2013 |
| JP | 2015503998 | 2/2015 |
| JP | 6117824 | 3/2017 |
| JP | 2017127669 | 7/2017 |
| JP | 2017537667 | 12/2017 |
| JP | 6408056 | 9/2018 |
| JP | 2018198983 | 12/2018 |
| JP | 2019503219 | 2/2019 |
| MX | 356582 | 6/2018 |
| RU | 2627390 | 8/2017 |
| WO | 03055611 | 7/2003 |
| WO | 2006063181 | 6/2006 |
| WO | 2008104573 | 9/2008 |
| WO | 2009091812 | 7/2009 |
| WO | 2011123441 | 10/2011 |
| WO | 2012003293 | 1/2012 |
| WO | 2013109930 | 7/2013 |
| WO | 2015029625 | 3/2015 |
| WO | 2015075141 | 5/2015 |
| WO | 2016053831 | 4/2016 |
| WO | 2017116707 | 7/2017 |

OTHER PUBLICATIONS

File History for U.S. Patent Application No. downloaded Jul. 30, 2019 (596 pages).

File History for European Patent Application No. downloaded Jul. 30, 2019 (151 pages).

File History for European Patent Application No. downloaded Jul. 30, 2019 (291 pages).

File History for European Patent Application No. downloaded Sep. 4, 2019 (233 pages).

"First Examination Report," for Indian Patent Application No. 6113/CHENP/2014 dated May 30, 2019 (4 pages).

"First Office Action," for Chinese Patent Application No. 2013800057179, dated Oct. 9, 2015 (7 pages) with English translation.

"International Preliminary Report on Patentability," for PCT Application No. PCT/US2015/052565 dated Apr. 13, 2017 (10 pages).

"International Preliminary Report on Patentability," for PCT Application No. PCT/US2016/066559 dated Jul. 12, 2018 (7 pages).

"International Preliminary Report on Patentability," for PCT/US2013/022202, dated Jul. 31, 2014 (5 pages).

"International Search Report & Written Opinion," for PCT/US2015/052565 dated Dec. 9, 2015 (14 pages).

"International Search Report and Written Opinion," for PCT Application No. PCT/US2016/066559 dated Sep. 6, 2017 (10 pages).

"International Search Report and Written Opinion," from PCT Application No. PCT/US2013/022202, dated Apr. 22, 2013 (9 pages).

Kroschwitz, J I. "Plastics," Concise Encyclopedia of Polymer Science and Engineering, John Wiley and Sons,1990, pp. 462-464.

"Office Action," for Canadian Patent Application No. 2,861,314 dated Jan. 15, 2019 (3 pages).

"Office Action," for Canadian Patent Application No. 2,861,314 dated Jul. 16, 2019 (3 pages).

"Office Action," for Japanese Patent Application No. 2014553466 dated Oct. 11, 2016 (5 pages) with English translation.

"Office Action," for Japanese Patent Application No. 2017-057269 dated Jan. 9, 2018 (8 pages) with English translation.

"Office Action," for Japanese Patent Application No. 2017-516919 dated Jun. 18, 2019 (16 pages) with English Translation.

"Office Action," for Mexican Patent Application No. MX/a/2014/008670 dated Sep. 3, 2017 (1 page), translation only.

"Office Action," for Russian Patent Application No. 2014133462 dated Nov. 17, 2016 (7 pages) with English translation.

"Preliminary Office Action," for Brazilian Patent Application No. 1120140176752 dated Aug. 20, 2019 (7 pages) with English Translation.

(56) References Cited

OTHER PUBLICATIONS

"Response to Office Action," for Canadian Patent Application No. 2,861,314 filed with CIPO Apr. 18, 2019 (32 pages).
"Communication Pursuant to Article 94(3) EPC," for European Patent Application No. 16871770.0 dated Oct. 7, 2019 (5 pages).
"Final Office Action," for U.S. Appl. No. 15/643,564 dated Dec. 16, 2019 (32 pages).
"Office Action Response," for Canadian Patent Application No. 2,861,314 filed Jan. 13, 2020 (17 pages).
"Office Action," for Japanese Patent Application No. 2017-516919 dated Dec. 24, 2019 (12 pages) with English Translation.
"Office Action," for Japanese Patent Application No. 2018-174717 dated Oct. 1, 2019 (10 pages) with English Translation.
"Response to Communication Pursuant to Article 94(3) EPC," for European Patent Application No. 15778502.3 filed Oct. 24, 2019 (9 pages).
"Response to Communication Pursuant to Article 94(3) EPC," for European Patent Application No. 16871770.0 filed with the EPO Jan. 29, 2020 (11 pages).
"Response to Examination Report," for Indian Patent Application No. 6113/CHENP/2014 filed Feb. 14, 2020 (10 pages).
"Response to Non-Final Rejection," dated Jun. 20, 2019 for U.S. Appl. No. 15/643,564, submitted via EFS-Web dated Sep. 20, 2019, 15 pages.
Shimizu, Hyoue et al., "Properties of Xylylene Diisocyanate and its Application for a Hardener of Paint," Journal of Network Polymer, Japan (2011) vol. 32, No. 6 pp. 310-316 (7 pages) with English Synopsis.
"Communication Pursuant to Article 94(3) EPC," for European Patent Application No. 16871770.0 dated Feb. 19, 2021 (5 pages).
"Final Office Action," for U.S. Appl. No. 15/643,564 dated May 6, 2020 (33 pages).
"First Office Action," for Chinese Patent Application No. 2016800810699 dated Jul. 15, 2020 (18 pages) with English Translation.
"Notice of Allowance," for U.S. Appl. No. 15/643,564 dated Sep. 15, 2020 (18 pages).
"Office Action," for Brazilian Patent Application No. 1120140176752 dated Feb. 5, 2021 (5 pages) English Translation only.
"Office Action," for Canadian Patent Application No. 2,861,314 dated Apr. 21, 2020 (3 pages).
"Office Action," for Japanese Patent Application No. 2018-534084 dated Nov. 10, 2020 (18 pages) with English Translation.
"Office Action," for Mexican Patent Application No. MX/a/2018/004036 dated Aug. 11, 2020 (5 pages) with English Summary.
"Office Action," for Mexican Patent Application No. MX/a/2018/007854 dated Jul. 23, 2020 (6 pages) with English Translation.
"Response to Final Office Action," for U.S. Appl. No. 15/643,564 filed with the USPTO Aug. 4, 2020 (10 pages).
"Response to Final Office Action," for U.S. Appl. No. 15/643,564 filed with the USPTO Mar. 19, 2020 (17 pages).
"Response to Office Action," for Canadian Patent Application No. 2,861,314 filed Aug. 5, 2020 (21 pages).

* cited by examiner

LUBRICIOUS COATINGS WITH SURFACE SALT GROUPS

This application is a continuation-in-part of U.S. patent application Ser. No. 15/375,442, filed Dec. 12, 2016, which claims the benefit of U.S. Provisional Application No. 62/272,440, filed Dec. 29, 2015, the contents of all of which are herein incorporated by reference.

FIELD

Embodiments herein relate to lubricious polymeric coatings. More specifically, embodiments herein relate to lubricious polymeric coatings for medical device having surface salt groups.

BACKGROUND

Medical devices include, amongst others, those that are chronically implanted, devices that are transitorily implanted, and those that not implanted at all. Many types of medical devices are enhanced by reducing the friction between the device and the environment that surrounds the medical device, particularly during insertion of a device. One example is catheters that are inserted, at least transitorily, into the body of a subject. Reduction of friction can lead to enhanced patient comfort, procedural ease for the care provider, reduced chances for infection, as well as reduced tissue disruption, amongst other benefits. One approach to reducing the friction between a medical device and the environment surrounding the medical device is to apply a lubricious coating onto the medical device.

SUMMARY

Embodiments herein include coated medical devices and coatings with salt groups. In an embodiment, a coated medical device is included, the coated medical device including a substrate and a polymeric layer disposed over the substrate. The polymeric layer includes a polymer and has an exterior surface. The coated medical device further includes a plurality of salt groups bonded to the polymer of the polymeric layer and disposed on the exterior surface of the polymeric layer. The salt groups can be the reaction product of a reactive group with an acid or base.

In an embodiment, a method of making a medical device is included. The method can include obtaining a medical device comprising a polymeric layer disposed over a substrate, the polymeric layer comprising an exterior surface with reactive groups disposed on the exterior surface. The method can further include applying a solution to the exterior surface. The solution can include an acid or a base. The acid or base in the solution reacts with the reactive groups to form salt groups.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Medical devices, especially those that are implanted in the body, are commonly subjected to a sterilization procedure to enhance safety. However, it was discovered that the sterilization procedure can adversely affect the lubricious nature of coatings. This is particularly true where the coatings are exposed to a higher temperature than ambient, such as during accelerated aging testing. In particular, it was observed that some sterilization procedures can make coatings with certain reactive groups less lubricious.

However, it was also discovered that contacting the reactive groups with an acid or a base to convert the reactive groups into salt groups was effective to preserve the lubricity of the coating through the sterilization process. For example, for coatings with carboxylic acid reactive groups, the application of a solution containing a base such as sodium bicarbonate or sodium hydroxide results in the formation of salt groups. Surprisingly, the salt groups allow the polymeric layer to retain its lubricity despite going through the sterilization procedure.

Figure 1:
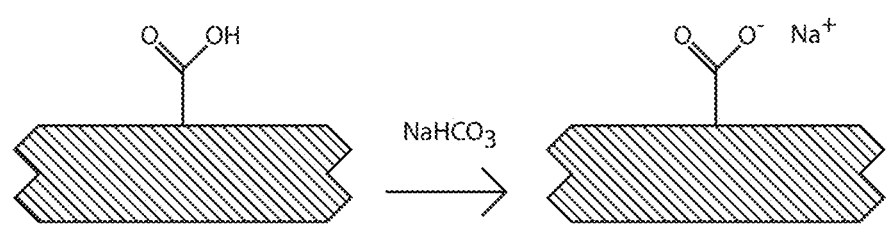
FIG. 1 is a diagram showing the formation of a salt group on the surface of a polymeric layer in accordance with various embodiments herein.

Referring now to FIG. 1, a diagram is shown of an exemplary reaction in accordance with various embodiments herein. In this view, a diagram is shown of a carboxylic acid on the surface of a polymeric layer. The carboxylic acid group can be a functional group of a polymer in the polymeric layer, such as poly(acrylic acid). The polymeric layer can include such reactive groups throughout its thickness, but it is shown in FIG. 1 only on the surface for ease of illustration. In this case, the carboxylic acid reacts with sodium bicarbonate leaving a salt group disposed on the surface.

It will be appreciated that while a carboxylic acid is illustrated in the diagram in FIG. 1, reactive groups herein can include various different groups. In some embodiments the reactive group can be an acid group. In some embodiments, the reactive group can be a carboxylic acid, a sulfonic acid, a sulfinic acid, a sulfate group, a phosphonic acid, a phosphonate group, a phosphate group, an amine, a weak acid group, or a weak base group. In some embodiments, more than one type of reactive group can be included. In other embodiments, only a single type of reactive group is included. In a particular embodiment, the reactive group is a carboxylic acid.

Depending on the nature of the reactive group, various acids or bases can be used in order to form the salt group. Exemplary bases can include both weak bases and strong bases. By way of example, exemplary bases can include, but are not limited to, metal carbonates such as sodium carbonate, sodium bicarbonate and potassium bicarbonate, metal hydroxides such as potassium hydroxide, sodium hydroxide, lithium hydroxide, and zinc hydroxide, ammonia, ammonium hydroxide, and amino acids having basic side chains such as arginine, lysine, and histidine. It will be appreciated that bases such as these can react with certain reactive groups, such as carboxylic acid groups, in order to form salt groups, or more specifically in the case of a carboxylic acid reactive group a carboxylate salt group.

It will be appreciated that treatment of carboxylic acid groups with a weak base such as a carbonate or bicarbonate metal salt can result in partial salt group formation (e.g., a partially salted form). In other words, less than all carboxylic acid groups will be converted into salt form. By way of example, in various embodiments herein, the salt form portion can be from about 10 to 99 percent of the carboxylic acid groups by number, or from about 40 to 99 percent of the carboxylic acid groups by number, or from 60 to 90 percent of the carboxylic acid groups by number, or from 70 to 95 percent of the carboxylic acid groups by number, or from 75 to 95 percent of the carboxylic acid groups by number. In some cases, the treated surface can retain trace amounts of carbonate. The salt form portion can be about 10, 15, 20, 25, 30, 40, 45, 50, 55, 60, 65, 70, 75, 80, 85, 90, 95, 98, or 99 percent of the carboxylic acid groups by number, or an amount falling within a range between any of the foregoing.

In various embodiments, the carboxylic acid groups treated herein can have a pKa from about 3.5 to 5. In some embodiments, the carboxylic acid groups can have a pKa from about 4.0 to 4.7. In some embodiments, the carboxylic acid groups can have a pKa from about 4.2 to 4.5. As described further below, in some embodiments the second polymeric layer or top layer can include an acrylic acid polymer that can be or include polyacrylic acid. Polyacrylic acid can have a pKa from 4.2 to 4.5.

Exemplary acids can include both weak acids and strong acids. Exemplary strong acids can include sulfuric acid, hydrochloric acid, nitric acid, perchloric acid, and the like. Exemplary weak acids can include carboxylic acids, such as $C_1$-$C_{20}$ carboxylic acids. Exemplary weak acids can specifically include acetic acid, p-toluenesulphonic acid, oxalic acid, maleic acid, citric acid, lactic acid, and the like. In various embodiments, the acid can include amino acids having acidic side chains such as aspartate and glutamate. It will be appreciated that, for example, sulfuric acid can react with an amine group in order to form an ammonium salt.

The salt group that results from a reaction between the reactive group and an acid or base depends on the nature of the reactants. However, in various embodiments, the salt group is a metal salt. In various embodiments, the salt group includes a cation selected from the group consisting of sodium, potassium, lithium, calcium, aluminum, zinc, magnesium and ammonium. In various embodiments, the salt group is a carboxylate salt.

The amount of the base or acid used can depend on various factors. In various embodiments, the acid or base is applied as a liquid acid or base solution. In some embodiments, a liquid acid or base solution is used having a concentration of the acid or base of at least 0.001 mM. In other embodiments, the concentration of the base or acid may sufficiently high so as to approach the solubility limits of the acid or base used in the particular solvent or solvent mixture of the solution at a given temperature, such as 21 degrees Celsius.

In some embodiments, the base or acid solution can be an aqueous solution. In some embodiments, the solution can include water and one or more additional solvent components. While not intending to be bound by theory, the addition of an additional component as part of the solution can speed drying of the applied acid or base solution where the additional component is more volatile than water. In some embodiments, the solution can include an alcohol. In some embodiments, the solution can include water and isopropyl alcohol.

The total amount of the acid or base applied per unit area of the coating to be treated can depend on factors such as the desired degree of conversion from reactive groups to salt groups. In some embodiments, a molar excess of an acid or base is applied as determined based on the number of reactive groups in the polymeric layer to which the acid or base solution is applied.

Many different techniques can be used to apply the acid or base solution to the substrate. By way of example, exemplary techniques can include drop coating, blade coating, dip coating, spray coating, and the like. In various embodiments, the acid or base solution is applied by dip coating. The speed of dip coating can vary. For example, the substrate can be dipped into the acid or base coating solution and then withdrawn at speeds between 0.01 and 10 cm/s.

In some embodiments, the acid or base solution can be rinsed off of the polymeric layer after it has had sufficient time to react with reactive groups on the polymeric layer. In other embodiments, a washing step can be omitted and the acid or base solution can be left on the polymeric layer. In various embodiments, a drying step can be included after the application of the acid or base solution and/or any rinsing steps.

Coatings and coated devices in accordance with embodiments herein can be processed in various ways in order to sterilize them. At the time of sterilization, the coatings and devices may or may not still have a remainder of acid or base solution (dried or not) disposed thereon. Many different methods of sterilization are contemplated herein. Sterilization approaches can include the application of heat, steam, pressure, irradiation (including, but not limited to, gamma ray irradiation, electron beam irradiation, and the like), chemicals (including, but not limited to ethylene oxide treatment, chlorine dioxide treatment, hydrogen peroxide sterilization, etc.), or the like. However, while not intending to be bound by theory, some techniques of sterilization (such as those involving very high temperatures) can potentially damage polymeric coatings. In an exemplary embodiment, the coatings or coated devices are processed using ethylene oxide treatment or electron beam irradiation. Ethylene oxide (EtO) is an alkylating agent that disrupts the DNA of microorganisms. EtO gas infiltrates packages and contacts the coatings or coated devices and kills the microorganisms. EtO treatment can include stages of pre-conditioning, sterilizer application, and degassing. Aspects of a type of EtO treatment can be found in U.S. Pat. No. 5,039,485, the content of which describing the process of EtO is herein incorporated by reference.

Coated medical devices in accordance with embodiments herein can have one or more polymeric layers. In some embodiments, only one polymeric layer includes a polymer with reactive groups. In other embodiments, more than one polymeric layer includes reactive groups. In some embodiments, the polymer layer with the reactive groups is disposed directly on the substrate of the medical device. In other embodiments, there can be one or more intermediate or tie layers disposed between the polymeric layer with the reactive groups and the substrate. A layer on the outside can be referred to as a top layer or top coat. Inner layers, of which there can be one or more, can be referred to as base layers. In some contexts, layers between a base layer and a top layer can be referred to as intermediate layers.

Figure 2:
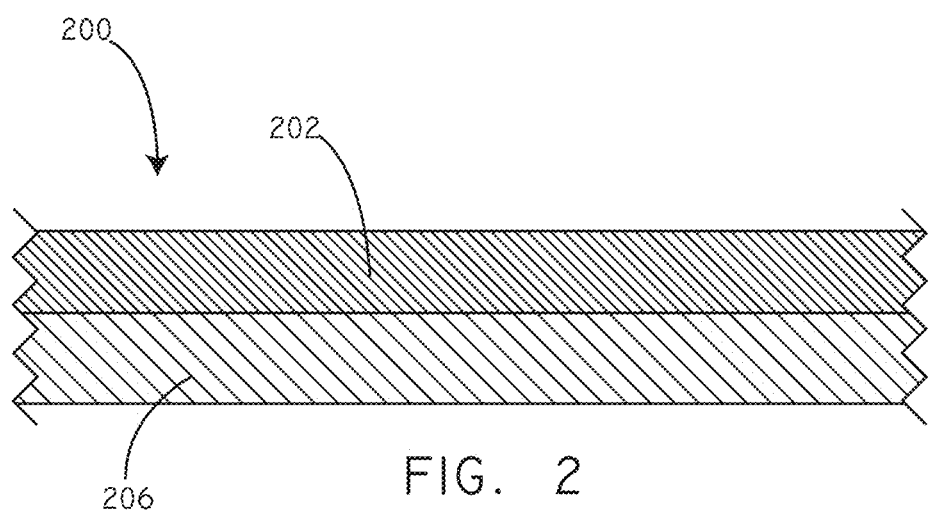
FIG. 2 is a schematic view of an embodiment of a coating.
Figure 3:
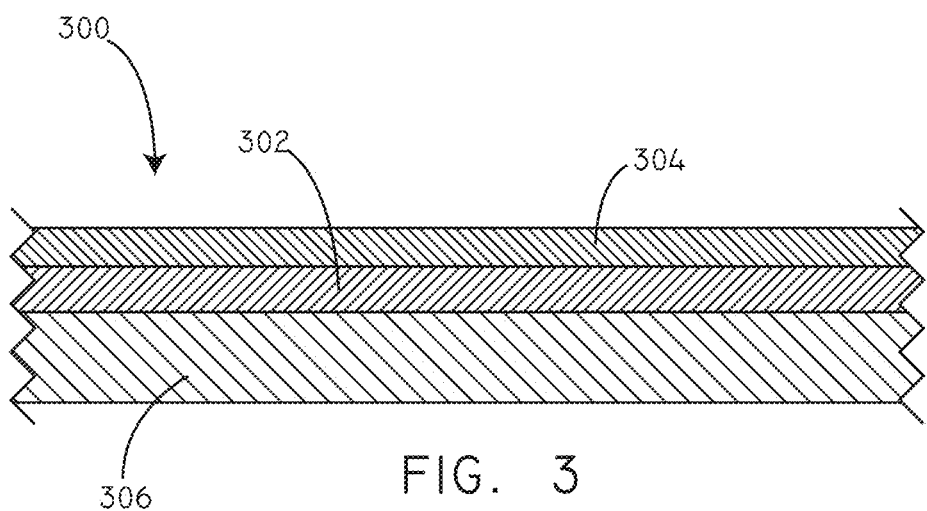
FIG. 3 is a schematic view of an embodiment of a coating.

Referring now to FIG. 2, a schematic cross-sectional view of a portion of a coated medical device 200 is shown in accordance with various embodiments herein. In this view, the medical device 200 includes a substrate 206 and a polymeric layer 202 disposed over the substrate 206. Exemplary substrate materials and polymeric layer materials are described below. The polymeric layer 202 in FIG. 2 can be equivalent to, and include the same materials as, the second polymeric layer 304 in FIG. 3. Referring now to FIG. 3, a schematic cross-sectional view of a portion of a coated medical device 300 coating on a substrate in accordance with various embodiments herein. The coating on the device 300 can include a base coating or first polymeric layer 302 and a top coating or second polymeric layer 304. The second polymeric layer 304 can be disposed on the first polymeric layer 302. In some embodiments, the second polymeric layer 304 is directly disposed on the first polymeric layer 302. In other embodiments, other components may be disposed in between the second polymeric layer 304 and the first polymeric layer 302. The first polymeric layer 302 can be disposed on a substrate 306. In some embodiments, the first polymeric layer 302 is directly disposed on substrate 306. In other embodiments, other components may be disposed in between the first polymeric layer 302 and the substrate 306.

The thickness of the first polymeric layer 202 and second polymeric layer 204 can vary. In some embodiments, the thickness of the first polymeric layer 202 and second polymeric layer 204, together, can be from about 100 nm to about 1000 nm when dry. In some embodiments, the thickness can be from about 200 nm to about 400 nm. In some embodiments, the thickness can be about 300 nm. For example, the thickness of the first polymeric layer, when dry, can be in the range of about 500 nm to about 5.0 µm, about 500 nm to about 2.0 µm, or about 1.0 µm to about 2.0 µm. For example, the thickness of the second polymeric layer, when dry, can be in the range of about 100 nm to about 5.0 µm, about 250 nm to about 5.0 µm, about 250 nm to about 1.0 µm, or about 1.0 µm to about 5.0 µm.

The coating can optionally be described in terms of the ratio of the thickness of a first vinyl pyrrolidone-containing polymeric layer to a second acrylic acid polymer-containing polymeric layer. For example, the ratio of the thickness can be in the range of about 50:1 to about 1:10 (first polymeric layer:second polymeric layer) (i.e., the first polymeric layer is about 50 times as thick as the second polymeric layer, or about one-tenth as thick as the second polymeric layer, or an amount in between 50× and $\frac{1}{10}^{th}$), about 20:1 to about 1:2, about 10:1 to about 1:1, or about 7.5:1 to about 2.5:1.

Exemplary materials for the polymeric layers herein (including the first polymeric layer and/or second polymeric layer) can be found in U.S. Publ. Pat. App. No. 2014/0193474.

In some embodiments, the first polymeric layer includes a vinyl pyrrolidone polymer. As used herein a "vinyl pyrrolidone polymer" refers to polymers including vinyl pyrrolidone monomeric units.

In some embodiments, the first polymeric layer includes a vinyl pyrrolidone polymer. As used herein a "vinyl pyrrolidone polymer" refers to polymers including vinyl pyrrolidone monomeric units. The vinyl pyrrolidone polymer can be a vinyl pyrrolidone homopolymer or a vinyl pyrrolidone copolymer including vinyl pyrrolidone and one or more (e.g., two, three, four, five, etc.) other monomeric units that are different than vinyl pyrrolidone. In embodiments, in a poly(vinyl pyrrolidone) copolymer, the vinyl pyrrolidone can be the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater, 92.5% (mol) or greater, 95% (mol) or greater, 97.5% (mol) or 99% (mol) or greater. In exemplary embodiments, vinyl pyrrolidone is present in the copolymer in the range of about 75% (mol) to about 97.5% (mol), about 85% (mol) to about 97.5% (mol), or about 90% (mol) to about 97.5% (mol).

Other monomers that can be copolymerized with vinyl pyrrolidone to provide the vinyl pyrrolidone polymer include, but are not limited to acrylamide, methacrylamide, acrylic acid, acrylamido-2-methylpropanesulfonate (AMPS), methacrylic acid, methyl acrylate, methyl methacrylate, hydroxyethyl methacrylate, hydroxyethyl acrylate, glyceryl acrylate, glyceryl methacrylate, ethylene glycol, and derivatives of these monomers.

For example, in some embodiments, the first polymeric layer includes a vinyl pyrrolidone polymer comprising a photoreactive group (e.g., photo-PVP). Reagents and methods for the preparation of photo-PVP can be found in references such as U.S. Pat. Nos. 4,979,959; 5,002,582; 5,263,992; 5,414,075; 5,512,329; and 5,637,460, the teaching of which are incorporated herein by reference. In some modes of practice, photo-PVP can be formed by the copolymerization of 1-vinyl-2-pyrrolidone and N-(3-aminopropyl (meth)acrylamide), which then can be derivatized with an acyl chloride (such as, for example, 4-benzoylbenzoyl chloride) under Schotten-Baumann conditions. That is, the acyl chloride reacts with the amino group of the N-(3-aminopropyl) moiety of the copolymer. An amide is formed resulting in the attachment of the aryl ketone to the polymer.

A vinyl pyrrolidone polymer comprising a photoreactive group can also be prepared by copolymerizing vinyl pyrrolidone with a monomer derivatized with a photoreactive group. Exemplary monomer derivatives include aryl ketone derivatives of hydrophilic free radically polymerizable monomers such as acrylamide, methacrylamide and AMPS. One exemplary methacrylamide-based monomer with a pendent photoreactive groups is N-[3-(4-benzoylbenzamido)propyl]methacrylamide (BBA-APMA), the synthesis which is described in Examples 1-3 of U.S. Pat. No. 5,858,653 (Duran et al.) Another exemplary methacrylamide-based monomer with a pendent photoreactive group is N-[3-(7-methyl-9-oxothioxanthene-3-carboxiamido)propyl]methacrylamide (MTA-APMA), the synthesis which is described in Examples 1-2 of U.S. Pat. No. 6,156,345 (Chudzik et al.)

Exemplary cross-linking agents comprising at least two photoreactive groups are described in greater detail herein.

Within the first polymeric layer, the components can be homogenously mixed in some embodiments.

In some embodiments, the first polymeric layer comprises a first cross-linking agent comprising at least two photoreactive groups, and amounts of the vinyl pyrrolidone polymer and a first cross-linking agent comprising at least two photoreactive groups at a weight ratio in the range of about 2:1 to about 30:1 (wt./wt.), respectively. In some embodiments, in the first polymeric layer the amounts of vinyl pyrrolidone polymer and the first cross-linking agent comprising at least two photoreactive groups are at a weight ratio in the range of about 2:1 to about 20:1 (wt./wt.), respectively. In some embodiments, in the first polymeric layer the amounts of vinyl pyrrolidone polymer and the first cross-linking agent comprising at least two photoreactive groups are at a weight ratio in the range of about 8:1 to about 20:1 (wt./wt.), respectively. In some embodiments, in the first polymeric layer the amounts of vinyl pyrrolidone polymer and the first cross-linking agent comprising at least two photoreactive groups are at a weight ratio in the range of about 8:1 to about 16:1 (wt./wt.), respectively. In some embodiments, in the first polymeric layer the amounts of vinyl pyrrolidone polymer and the first cross-linking agent comprising at least two photoreactive groups are at a weight ratio of about 18:1 (wt./wt.), respectively. In some embodiments, all components of the base coating comprise photoreactive groups.

In some embodiments, the first polymeric layer includes a vinyl pyrrolidone polymer without photoreactive groups (e.g., non-ionic, underivatized PVP). The underivatized PVP can be of various molecular weights. In some embodiments, the first polymeric layer has amounts of vinyl pyrrolidone polymer comprising a photoreactive group, non-derivatized vinyl pyrrolidone polymer, and first cross-linking agent comprising at least two photoreactive groups at a weight ratio in the range of about 8:0.1:0.1 to 13:8:1 (wt./wt./wt.), respectively. In some embodiments, the first polymeric layer has amounts of vinyl pyrrolidone polymer comprising a photoreactive group, non-derivatized vinyl pyrrolidone polymer, and first cross-linking agent comprising at least two photoreactive groups at a weight ratio of about 13:5:1 (wt./wt./wt.). In some embodiments, the first polymeric layer has amounts of non-derivatized vinyl pyrrolidone polymer and first cross-linking agent comprising at least two photoreactive groups at a weight ratio in the range of about 0.1:0.5 to 8:1 (wt./wt.), respectively.

In yet other embodiments the first polymeric layer can have other non-ionic exemplary polymers that include, but are not limited to, poly(N-vinyl caprolactam), polymers containing ether groups such as poly(ethylene oxide) (PEO), poly(propylene oxide) (PPO), poly(propylene glycol) (PPG) poly(vinyl methyl ether), or blends or copolymers thereof and non-ionic acrylic type polymers such as polyacrylamide, poly(N-isopropylacrylamide), and poly(N,N-dimethylacrylamide).

Other representative non-ionic exemplary polymers include, but are not limited to, polymeric alcohols such as poly(vinyl alcohol) (PVA), poly(2-hydroxyehtylacrylate) (PHEA) and poly(2-hydroxyethyl vinyl ether) PHEVE), poly(2-ethyl-2-oxazoline) (PEOX), poly(n-acetyliminoethylene) (PAIE) and water soluble polysaccharides such as methyl cellulose, hydroxypropyl cellulose and hydroxyethylcellulose. (see "Hydrogen-Bonded Interpolymer Complexes; Formation, Structure and Applications" Chapters 1 and 7, Eds. Vitaliy V. Khutoryanskiy and Georgios Stalkos (2009).

The second polymeric layer or top coat can include an acid group-containing polymer. An "acid group-containing polymer" refers to polymer that has acid groups presented on the polymer chain. Acidic groups include, for example, sulfonic acids, carboxylic acids, phosphonic acids, and the like. Exemplary salts of such groups include, for example, sulfonate, carboxylate, and phosphate salts. Exemplary counter ions include alkali, alkaline earths metals, ammonium, protonated amines, and the like. If one or more counter ions are used, the acid groups of the acid group-containing polymer are partially neutralized. For example a molar percentage of the acid groups can be neutralized with counter ions, such as in the range of x to y, wherein x to y are selected from about 1%, 5%, 10%, 15%, 20%, 25%, 30%, 40%, 50%, 60%, 70%, 80%, or 90%, wherein x is less than y.

Exemplary carboxylic acid-group containing monomers that can be used to prepare the acid group-containing polymer, include, but are not limited to acrylic acid, methacrylic acid, itaconic acid, monomethyl itaconic acid, maleic anhydride, fumaric acid, and crotonic acid, and salts thereof. Exemplary sulfonic acid-group containing monomers that can be used to prepare the acid group-containing polymer, include, but are not limited to acrylamido-2-methylpropanesulfonic acid (AMPS), 2-(meth)acrylamido-2-methylpropane sulfonic acid, vinyl sulfonic acid, 2-sulfoethyl methacrylate, and salts thereof. Copolymers made from a combination of two or more different acid-group containing monomers can be used, or copolymers made from one or more acid-group containing monomers and one or more non-acid group containing monomers can be used. These copolymers can be random copolymers, block copolymers, graft copolymers or blends thereof to achieve the desired outcome.

Other exemplary carboxylic acid-containing monomers that can be used to prepare the acid group-containing copolymers include styrene and maleic anhydride copolymerized to produce styrene-maleic anhydride copolymer (PSMA). Yet other exemplary carboxylic acid-containing monomers are described in "Hydrogen-Bonded Interpolymer Complexes; Formation, Structure and Applications" Chapters 1 and 7, Eds. Vitaliy V. Khutoryanskiy and Georgios Stalkos (2009).

The acid group-containing polymer may optionally be described with reference to its pH. For example, the acid group-containing polymer may have a pH in the range of about 1 to about 5, about 1.2 to about 5, about 1.5 to about 5, about 2.5 to about 5, about 2.75 to about 4.5, or about 3 to about 4.25.

In some embodiments, the second polymeric layer can include hyaluronic acid, either as a homopolymer or as part of a copolymer including one or more other subunits that are different than hyaluronic acid.

In some embodiments, the second polymeric layer or top coat can include a basic group-containing polymer. A "basic group-containing polymer" refers to polymer that has basic groups presented on the polymer chain. Basic groups include, for example, amine groups, and the like. By way of example, in some embodiments the second polymeric layer can include one or more of polyethylenimine (PEI) or polyvinylamine (PVAm) either as a homopolymer or as part of a copolymer including one or more other subunits that are different.

The second polymeric layer that is a top coating can comprise an acrylic acid polymer. As used herein an "acrylic acid polymer" refers to polymers including acrylic acid monomeric units. The acrylic acid polymer can be an acrylic acid homopolymer or an acrylic acid copolymer including acrylic acid and one or more (e.g., two, three, four, five, etc.) other monomeric units that are different than acrylic acid. In embodiments, in a poly(acrylic acid) copolymer, the acrylic acid can be the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater, 92.5% (mol) or greater, 95% (mol) or greater, 97.5% (mol) or 99% (mol) or greater. In exemplary embodiments, acrylic acid is present in the copolymer in the range of about 75% (mol) to about 100% (mol), about 85% (mol) to about 100% (mol), about 95% (mol) to about 100% (mol), or about 98% (mol) to about 100% (mol).

In some embodiments, the acrylic acid polymer in the top coating may have an average molecular weight of 150 kDa or greater. In yet other embodiments the acrylic acid polymer in the top coating may have an average molecular weight of 250 kDa or greater, 350 kDa, 450 kDa, 550 kDa, 650 kDa or greater or even in some cases an average molecular weight of 750 kDa or greater.

In some modes of preparation, the acrylic acid polymer is prepared by free radical polymerization of acrylic acid at (e.g, about a 0.8 M concentration) in deionized water. In modes where a portion of the acid groups are neutralized, a concentrated base such as NaOH is added to the acrylic acid solution. Next, an initiator such as ammonium persulfate is added with stirring. The polymerization solution can be degassed with nitrogen and stirred for hours (e.g., 12-24 hours) at an elevated temperature (e.g., greater than 50° C.). The polymer can then be polymerized against continuous flow deionized water using 12-14 K dialysis tubing, and then isolated by lyophilization.

The acrylic acid polymer of the second polymeric layer can undergo hydrogen bonding with the vinyl pyrrolidone polymer of the first polymeric layer. More specifically, hydrogen bonding between the polymers can involve the carbonyl oxygens of both the pyrrolidone ring and the carboxylic acid.

In other embodiments, the second polymeric layer that is a top coating also includes a second cross-linking agent comprising at least two photoreactive groups, or an acrylamide polymer comprising at least one photoreactive group. The second cross-linking agent may be the same or different than the first cross-linking agent. In some embodiments, the acrylamide polymer can comprise acrylamide, acrylamido-2-methylpropanesulfonate groups (AMPS), and poly(ethyleneglycol) groups. For example, in a specific embodiment, the acrylamide polymer can be N-acetylated poly[acrylamide-co-sodium-2-acrylamido-2-methylpropanesulfonate-co-N-(3-(4-benzoylbenzamido)propyl) methacrylamide]-co-methoxy poly(ethylene glycol) monomethacrylate. Reagents and method for the preparation of polymers comprising polyacrylamide in accordance with embodiments herein can be found in can be found in references such as U.S. Pat. Nos. 4,979,959; 5,002,582; 5,263,992; 5,414,075; 5,512,329; and 5,637,460, the content of which are incorporated herein by reference.

In some embodiments, some of the components of the second polymeric layer that is the top coating comprise photoreactive groups. In some embodiments, the second polymeric layer that is the top coating has amounts of acrylic acid polymer and acrylamide polymer at a ratio in the range of about 2:1 to about 1:2 (wt./wt.), respectively. In some embodiments, the second polymeric layer that is the top coating has amounts of acrylic acid polymer and second cross-linking agent comprising at least two photoreactive groups at a ratio of about 13:1 (wt./wt.). Within the second polymeric layer that is the top coating, the components can be homogenously mixed in some embodiments.

If desired, the coating can be analyzed to determine one or more coating properties. For example, the microscopy can be carried out to determine coating quality and coating thickness. In some embodiments, the coating has a thickness in the range of about 500 nm to about 10 µm, about 750 nm to about 7.5 µm, or about 1 µm to about 5 µm. Coating properties such as lubricity can be measured, as well as analysis of particulate levels.

The coating exhibits lubricity that may be observed as relative low friction. In some embodiments, the coating can be lubricious after exposure to water. The coating may exhibit lubricity of between 0 and 30 grams of force when wetted as measured by a vertical pinch test, such as that described below. In some embodiments, the coating may exhibit lubricity of less than about 20 grams of force when wetted. In some embodiments, the coating may exhibit lubricity of less than about 15 grams of force when wetted.

In various embodiments, the coating may be described in terms of durability of the lubricity. For example, the lubricity may be retained over an extended period of time when the coating is exposed to frictional forces. For example, in some embodiments, lubricity may be maintained over a plurality of frictional testing cycles. In some embodiments, the coating may exhibit a lubricity of between 0 and 30 grams of force when wetted for at least 10 consecutive testing cycles. In some embodiments, such as where at least 15 frictional test cycles are performed, the measured lubricity will increase no more than 30% between the average of cycles 1-5 and the average of cycles 10-15 of the testing.

The coating may exhibit a relatively low amount of particulate release when exposed to an aqueous environment. A description of particulate levels can be based on a predetermined coating area and thickness. In one mode of measurement the particle counts are based on 600 mm$^2$ of coated surface having a coating thickness in the range of 500 nm to 10 µm. However, it is understood that the particle count can be based on coating areas of greater or less than 600 mm$^2$. For example, the coating will generate less than 20,000 particles of greater than 10 microns in size in an aqueous environment. In some embodiments, the coating will generate less than 10,000 particles of greater than 10 microns in size in an aqueous environment. In some embodiments, the coating will generate less than 5,000 particles of greater than 10 microns in size in an aqueous environment. In some embodiments, the coating will generate less than 3,000 particles of greater than 10 microns in size in an aqueous environment. In some embodiments, the coating will generate less than 1,000 particles of greater than 10 microns in size in an aqueous environment. It will be appreciated that in accordance with various embodiments herein, the properties of lubricity and low particulate release are both present.

In some embodiments the coating has a particle count (particle sizes measured at greater than 10 µm) in the range of 500 to 10,000, in the range of 500 to 7500, in the range of 500 to 6000, in the range of 500 to 5000, in the range of 500 to 4500, in the range of 500 to 4000, in the range of 500 to 3750, in the range of 500 to 3500, in the range of 500 to 3250, or in the range of 500 to 3000, in the range of 800 to 1500, in the range of 1200 to 2000, in the range of 1500 to 3000, in the range of 2000 to 4500, in the range of 3000 to 4000, in the range of 100 to 500, or in the range of 3000 to 5000, per 600 mm² of coated surface having a coating thickness in the range of 100 nm to 10 µm.

Testing of the particulates generated in aqueous solution for the embodiments herein can be performed according to the following procedure. As a derivative of the procedures described in ASTM F2394, substrates can be passed through a tortuous path in an aqueous solution.

In some embodiments, the first polymeric layer including the vinyl pyrrolidone polymer and/or the second polymeric layer including the acrylic acid polymer can have a hemo-compatible (blood compatible) property. For example, a medical article with a hemocompatible coating can reduce effects that may associated with placing a foreign object in contact with blood components, such as the formation of thrombus or emboli (blood clots that release and travel downstream). The hemocompatible property of the coating can be observed as compared to a medical device that does not have the coating. Optionally, the coating can be further modified with hemocompatible proteins or peptides as discussed herein to enhance the hemocompatible (blood compatible) property.

An assay for measuring hemocompatibility of a coated surface can be performed using any one of a variety of tests. Techniques, such as including clot-based tests, such an artificial circulation (Chandler loop) using whole blood augmented with platelets (e.g., see Robbie, L. A., et al. (1997) Thromb Haemost. 77:510-5), or the in-vitro bovine blood loop, chromogenic or color assays, direct chemical measurements, and ELISAs, are used for coagulation testing (e.g., see, Bates, S. M., and Weitz, J. I. (2005) Circulation, 112:53-60; and Walenga, J. M., et al. (2004) Semin Thromb Hemost. 30:683-695). Whereas clotting assays provide a global assessment of coagulation function, chromogenic tests are designed to measure the level or function of specific factors.

As used herein, the phrases "latent photoreactive group" and "photoreactive group" are used interchangeably and refer to a chemical moiety that is sufficiently stable to remain in an inactive state (i.e., ground state) under normal storage conditions but that can undergo a transformation from the inactive state to an activated state when subjected to an appropriate energy source. Unless otherwise stated, references to photoreactive groups herein shall also include the reaction products of the photoreactive groups. Photoreactive groups respond to specific applied external stimuli to undergo active specie generation with resultant covalent bonding to an adjacent chemical structure. For example, in an embodiment, a photoreactive group can be activated and can abstract a hydrogen atom from an alkyl group. A covalent bond can then form between the compound with the photoreactive group and the compound with the C—H bond. Suitable photoreactive groups are described in U.S. Pat. No. 5,002,582, the disclosure of which is incorporated herein by reference.

Photoreactive groups can be chosen to be responsive to various portions of actinic radiation. Typically, groups are chosen that can be photoactivated using either ultraviolet or visible radiation. Suitable photoreactive groups include, for example, azides, diazos, diazirines, ketones, and quinones. The photoreactive groups generate active species such as free radicals including, for example, nitrenes, carbenes, and excited states of ketones upon absorption of electromagnetic energy.

In some embodiments, the photoreactive group is an aryl ketone, such as acetophenone, benzophenone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive groups include quinones such as, for example, anthraquinone.

The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. If a reactive bond (e.g., carbon/hydrogen) is not available for bonding, the ultraviolet light-induced excitation of the benzophenone group is reversible and the molecule returns to ground state energy level upon removal of the energy source. Photoreactive aryl ketones such as benzophenone and acetophenone can undergo multiple reactivations in water and hence can provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate.

Other photoreactive groups include the diazirines (—$CHN_2$) such as 3-trifluoromethyl-3-phenyldiazirine; and ketenes (—CH=C=O) such as ketene and diphenylketene.

In particular embodiments, the photoreactive groups are aryl ketones, such as benzophenone.

Cross-linking agents used in accordance with embodiments herein can include those with at least two photoreactive groups. Exemplary cross-linking agents are described in U.S. Publ. Pat. App. No. 2011/0245367, the content of which is herein incorporated by reference in its entirety. In some embodiments, the first and/or second crosslinking agents have a molecular weight of less than about 1500 kDa. In some embodiments, the crosslinking agent can have a molecular weight of less than about 1200, 1100, 1000, 900, 800, 700, 600, 500, or 400.

In some embodiments, at least one of the first and/or second cross-linking agents may comprise a linking agent having formula $Photo^1$-LG-$Photo^2$, wherein $Photo^1$ and $Photo^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and/or second cross-linking agents comprises a linking agent having a formula selected from (a):

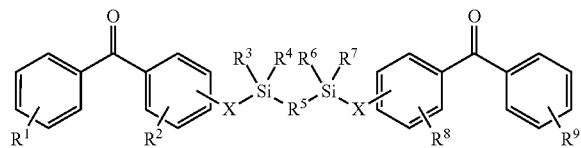

wherein $R^1$, $R^2$, $R^8$ and $R^9$ are any substitution; $R^3$, $R^4$, $R^6$ and $R^7$ are alkyl, aryl, or a combination thereof; $R^5$ is any substitution; and each X, independently, is O, N, Se, S, or alkyl, or a combination thereof; (b):

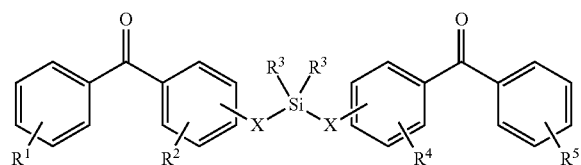

wherein $R^1$ and $R^5$ are any substitution; $R^2$ and $R^4$ can be any substitution, except OH; $R^3$ can be alkyl, aryl, or a combination thereof; and each X, independently, is O, N, Se, S, alkyl, or a combination thereof; (c):

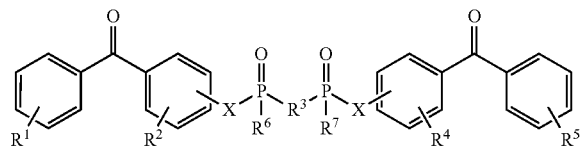

wherein $R^1$, $R^2$, $R^4$ and $R^5$ are any substitution; $R^3$ is any substitution; $R^6$ and $R^7$ are alkyl, aryl, or a combination thereof; and each X, independently, is O, N. Se, S, alkyl, or a combination thereof; and (d):

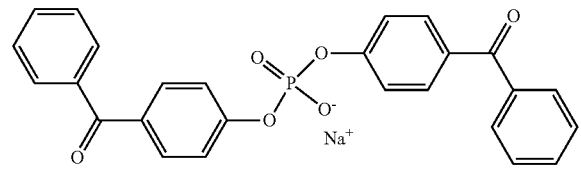 [SMILES: O=C(c1ccccc1)c1ccc(OP(=O)([O-])Oc2ccc(C(=O)c3ccccc3)cc2)cc1 ; [Na+]]

In other embodiments, the first and/or second cross-linking agent(s) can be an ionic photocrosslinking agent having good solubility in an aqueous composition, such as the first and/or second coating composition used to prepare the first polymeric layer and/or second polymeric layer. Thus, in some embodiments, at least one ionic photoactivatable cross-linking agent is used to form the coating. In some cases, an ionic photoactivatable cross-linking agent can crosslink the polymers within the second coating layer which can also improve the durability of the coating.

Any suitable ionic photoactivatable cross-linking agent can be used. In some embodiments, the ionic photoactivatable cross-linking agent is a compound of formula I: $X^1$—Y—$X^2$ where Y is a radical containing at least one acidic group, basic group, or a salt of an acidic or basic group. $X^1$ and $X^2$ are each independently a radical containing a latent photoreactive group. The photoreactive groups can be the same as those described herein. Spacers can also be part of $X^1$ or $X^2$ along with the latent photoreactive group. In some embodiments, the latent photoreactive group includes an aryl ketone or a quinone.

The radical Y in formula I can provide desired water solubility for the ionic photoactivatable cross-linking agent. The water solubility (at room temperature and optimal pH) can be at least about 0.05 mg/mL. In some embodiments, the solubility is about 0.1 mg/mL to about 10 mg/mL or about 1 mg/mL to about 5 mg/mL.

In some embodiments of formula I, Y is a radical containing at least one acidic group or salt thereof. Such a photoactivatable cross-linking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic cross-linking agent includes a sulfonic acid or sulfonate group.

Suitable counter ions include alkali, alkaline earths metals, ammonium, protonated amines, and the like.

For example, a compound of formula I can have a radical Y that contains a sulfonic acid or sulfonate group; $X^1$ and $X^2$ can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy) benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; $X_1$ and $X_2$ can contain photoreactive groups that include aryl ketones. Such photoactivatable cross-linking agents include ethylenebis(4-benzoylbenzyldimethylammonium) salt; hexamethylenebis (4-benzoylbenzyldimethyl-ammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyl-dimethylammonio)ethyl]-4-benzoylbenzylmethylammonium salt; 4,4-bis(4-benzoylbenzyl)morpholinium salt; ethylenebis[(2-(4-benzoylbenzyldimethyl-ammonio)ethyl)-4-benzoylbenzylmethylammonium] salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable cross-linking agent can be a compound having the formula:

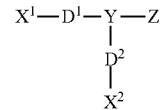

wherein $X^1$ includes a first photoreactive group; $X^2$ includes a second photoreactive group; Y includes a core molecule; Z includes at least one charged group; $D^1$ includes a first degradable linker; and $D^2$ includes a second degradable linker. Exemplary degradable ionic photoactivatable cross-linking agents are described in US Patent Application Publication US 2011/0144373 (Swan et al., "Water Soluble Degradable Crosslinker"), the disclosure of which is incorporated herein by reference.

In some aspects a non-ionic photoactivatable cross-linking agent can be used. In one embodiment, the non-ionic photoactivatable cross-linking agent has the formula $XR^1R^2R^3R^4$, where X is a non-ionic chemical backbone, and $R^1$, $R^2$, $R^3$, and $R^4$ are radicals that include a latent photoreactive group. Exemplary non-ionic cross-linking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable cross-linking agent can be represented by the formula: $PG^2$-$LE^2$-X-$LE^1$-$PG^1$, wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof, $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Exemplary non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Further embodiments of non-ionic photoactivatable cross-linking agents can include, for example, those described in U.S. Provisional Application 61/494,724 filed Jun. 8, 2011 (now U.S. application Ser. No. 13/490,994) (Swan et al., "Photo-Vinyl Primers/Crosslinkers"), the disclosure of which is incorporated herein by reference. Exemplary cross-linking agents can include non-ionic photoactivatable cross-linking agents having the general formula $R^1$—X—$R^2$, wherein $R^1$ is a radical comprising a vinyl group, X is a radical comprising from about one to about twenty carbon atoms, and $R^2$ is a radical comprising a photoreactive group.

Other exemplary non-ionic cross-linking agents include those formed by a mixture of the chemical backbone molecule (such as pentaerythritol) and an excess of a derivative of the photoreactive group (such as 4-bromomethylbenzophenone). An exemplary product is tetrakis(4-benzoylbenzyl ether) of pentaerythritol (tetrakis(4-benzoylphenylmethoxymethyl)methane). See U.S. Pat. Nos. 5,414,075 and 5,637,460.

A single photoactivatable cross-linking agent or any combination of photoactivatable cross-linking agents can be used in forming the coating. In some embodiments, at least one nonionic cross-linking agent such as tetrakis(4-benzoylbenzyl ether) of pentaerythritol can be used with at least one ionic cross-linking agent. For example, at least one non-ionic photoactivatable cross-linking agent can be used with at least one cationic photoactivatable cross-linking agent such as an ethylenebis(4-benzoylbenzyldimethylammonium) salt or at least one anionic photoactivatable cross-linking agent such as 4,5-bis(4-benzoyl-phenylmethyleneoxy)benzene-1,3-disulfonic acid or salt. In another example, at least one nonionic cross-linking agent can be used with at least one cationic cross-linking agent and at least one anionic cross-linking agent. In yet another example, a least one cationic cross-linking agent can be used with at least one anionic cross-linking agent but without a non-ionic cross-linking agent.

An exemplary cross-linking agent is disodium 4,5-bis[(4-benzoylbenzyl)oxy]-1,3-benzenedisulfonate (DBDS). This reagent can be prepared by combining 4,5-dihydroxybenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

A further exemplary cross-linking agent is ethylenebis(4-benzoylbenzyldimethylammonium) dibromide. This agent can be prepared as described in U.S. Pat. No. 5,714,360, the content of which is herein incorporated by reference.

Further cross-linking agents can include the cross-linking agents described in U.S. Publ. Pat. App. No. 2010/0274012 and U.S. Pat. No. 7,772,393 the content of all of which is herein incorporated by reference.

In some embodiments, cross-linking agents can include boron-containing linking agents including, but not limited to, the boron-containing linking agents disclosed in U.S. 61/666,516, entitled "Boron-Containing Linking Agents" by Kurdyumov et al., the content of which is herein incorporated by reference. By way of example, linking agents can include borate, borazine, or boronate groups and coatings and devices that incorporate such linking agents, along with related methods. In an embodiment, the linking agent includes a compound having the structure (I):

(I)

wherein $R^1$ is a radical comprising a photoreactive group; R is selected from OH and a radical comprising a photoreactive group, an akyl group and an aryl group; and $R^3$ is selected from OH and a radical comprising a photoreactive group. In some embodiments the bonds B—$R^1$, B—$R^2$ and B—$R^3$ can be chosen independently to be interrupted by a heteroatom, such as O, N, S, or mixtures thereof.

Additional agents for use with embodiments herein can include stilbene-based reactive compounds including, but not limited to, those disclosed in U.S. 61/736,436, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, cross-linking agents, hydrophilic coatings, and associated reagents are disclosed in US2011/0059874; US 2011/0046255; and US 2010/0198168, the content of all of which is herein incorporated by reference.

In some embodiments, a base or first coating solution is formed by including a vinyl pyrrolidone polymer, optionally one or more other compounds, in a solvent. For example, the solvent can comprise a vinyl pyrrolidone polymer, having a pendent photoreactive group, or the solvent can comprise a non-derivatized vinyl pyrrolidone polymer and a first cross-linking agent comprising at least two photoreactive groups. In some embodiments, the first coating solution can also include a mixture of a non-derivatized vinyl pyrrolidone polymer and a vinyl pyrrolidone polymer, having a pendent photoreactive group.

In some embodiments, the solvent for the first coating solution can include water and isopropyl alcohol (IPA). The proportion of IPA to water (vol:vol) can be in the range of about 95% IPA-5% water to about 10% IPA-90% water. For example, in some embodiments, the amount of IPA:water can a ratio of about 95:5, 90:10, 85:15, 80:20, 75:25, 70:30, 65:35, 60:40, 55:45, 50:50, 45:55, 40:60, 35:65, 30:70, 25:75, 20:80, 15:85, or 10:90 (vol:vol), or can be within a range with endpoints including any two of those ratios such that the total relative portions of IPA and water are equal to 100. In some embodiments, the solvent can include about 75% isopropyl alcohol and about 25% water.

In some embodiments, top or second coating solution is formed by including the arcrylic acid polymer in a solvent. Other compound can optionally be included in the solvent. For example, the compounds can include the acrylic acid polymer, a second cross-linking agent comprising at least two photoreactive groups, a polymer comprising polyacrylamide, or a polymer derivatized with at least one photoreactive group.

In some embodiments, the solvent for the second coating solution can include water and isopropyl alcohol (IPA). The proportion of IPA to water (vol:vol) can be in the range of 0% IPA-100% water to about 60% IPA-40% water. For example in some embodiments, the amount of IPA:water can be a ratio of about 0:100, 5:95, 10:90, 15:85, 20:80, 25:75, 30:70, 35:65, 40:60, 45:55, 50:50, 55:45, 60:40 (vol:vol), or can be within a range with endpoints including any two of those ratios such that the total relative portions of IPA and water are equal to 100. In some embodiments, the solvent can include about 15% isopropyl alcohol and about 85% water.

The viscosity of the solutions can vary. In some embodiments, the viscosity of the second solution is less than about 100 centipoise (cP). In some embodiments, the viscosity of the second solution is equal to or less than about 90, 80, 70 60, 50, 40, 30, 20, or 10 cP.

The first coating solution can be applied to a substrate. Prior to application of the first coating solution to the substrate, one or more of many different pretreatment steps can be taken. In some embodiments, the surface of the substrate can be cleaned. For example, the surface can be wiped or dipped into an alcohol such as isopropyl alcohol. In some embodiments, the substrate can be put into a detergent solution such as a VALTRON solution and sonicated. In some embodiments, a compound can be disposed on the surface of the substrate to act as a tie layer. In some embodiments the surface of the substrate can be sterilized.

Many different techniques can be used to apply the solution to the substrate. By way of example, exemplary techniques can include drop coating, blade coating, dip coating, spray coating, and the like. In various embodiments, the solution is applied by dip coating. The speed of dip coating can vary. For example, the substrate can be dipped into the base coating solution and then withdrawn at speeds between 0.01 and 10 cm/s. In some embodiments, the substrate can be dipped into the base coating solution and then withdrawn at speeds between 0.1 and 4 cm/s. In some embodiments, the substrate can be dipped into the first coating solution and then withdrawn at speeds between 0.1 and 2 cm/s. In some embodiments, the substrate can be dipped into the first coating solution and then withdrawn at speeds between 0.1 and 1.5 cm/s. In some embodiments, the substrate can be dipped into the first coating solution and then withdrawn at speeds between 0.1 and 1 cm/s. In some embodiments, the substrate can be dipped into the first coating solution and then withdrawn at speeds between 0.1 and 0.5 cm/s. In some embodiments, the substrate can be withdrawn at speeds between 0.2 and 0.4 cm/s. In some embodiments, the substrate can be withdrawn at speeds of about 0.3 cm/s.

After the first coating solution is applied to the substrate, actinic radiation such as UV radiation, can be applied to activate photoreactive groups within the components of the first coating solution forming the base layer. Actinic radiation can be provided by any suitable light source that promotes activation of the photoreactive groups. Preferred light sources (such as those available from Dymax Corp.) provide UV irradiation in the range of 190 nm to 360 nm. An exemplary UV light source is a Dymax 2000-EC series UV flood lamp with a 400 Watt metal halide bulb. A suitable dose of radiation is in the range of from about 0.5 mW/cm$^2$ to about 2.0 mW/cm$^2$. Optionally, the base coating solution can be dried, before or after application of the actinic radiation.

The second coating solution can be applied on top of the first polymeric layer. Many different techniques can be used to apply the solution to the substrate. In a particular embodiment, the solution is applied by dip coating. The speed of dip coating can vary. For example, the substrate can be dipped into the second coating solution and then withdrawn at speeds between 0.01 and 10 cm/s. In some embodiments, the substrate can be dipped into the second coating solution and then withdrawn at speeds between 0.1 and 4 cm/s. In some embodiments, the substrate can be dipped into the second coating solution and then withdrawn at speeds between 0.1 and 0.5 cm/s. In some embodiments, the substrate can be withdrawn at speeds between 0.2 and 0.4 cm/s. In some embodiments, the substrate can be withdrawn at speeds of about 0.3 cm/s.

In other embodiments, a coating composition including an acrylic acid polymer is applied to a device material formed by the extrusion of a composition that includes a vinyl pyrrolidone polymer and a thermoplastic, such as PEBAX. Implantable or insertable medical devices, or portions thereof, made using an extrusion process are described herein, and are also known in the art.

The coating composition applied to the extruded material may include a second cross-linking agent comprising at least two photoreactive groups, a polymer comprising polyacrylamide, or a polymer derivatized with at least one photoreactive group. In this embodiment, the extruded material containing a vinyl pyrrolidone polymer (on which the acrylic acid polymer coating is applied) can be considered a "device material" as opposed to a "first polymeric layer" or "base coat" that includes the vinyl pyrrolidone polymer, according to other embodiments of the disclosure.

In this embodiment, the polymeric layer including the acrylic acid polymer is directly in contact with the extruded material of the device that includes the vinyl pyrrolidone polymer and a thermoplastic. The polyacrylic acid coating on the extruded material can consist of a single polymeric layer including the polyacrylic acid, or can optionally include more than one polymeric layer, with the polyacrylic acid-containing layer present between the extruded vinyl pyrrolidone polymer/thermoplastic material of the device, and any other optional layer(s) in the coating.

The polymeric layer including the acrylic acid polymer can be formed on the extruded vinyl pyrrolidone polymer/thermoplastic material of the device using one or more techniques. In some modes of practice the coating composition is applied by dip coating, such as by dip coating a device formed from extruded vinyl pyrrolidone polymer/thermoplastic polymeric material according to the dip coating techniques as described herein.

In other modes of practice, the polymeric layer including the acrylic acid polymer can be formed on the extruded material surface as the extruded device exits the extrusion apparatus. For example one method for preparing the coated device includes a step of extruding a composition comprising vinyl pyrrolidone polymer and a thermoplastic polymer, using extrusion equipment to form all or a portion of an extruded device. For example, the extruded device may be in the form of a tube, or extrusion may form a thin extruded layer on the preformed tube, or a coextruded tube. The extruded device includes a portion (surface) made of vinyl pyrrolidone polymer and a thermoplastic that comes into contact with the liquid solution containing a polyacrylic acid (e.g., a "coating bath"). The liquid solution can provide a dual role in the process, cooling the extruded material and providing a coating bath of polyacrylic acid. The rate of movement of the extruded material through the coating bath of polyacrylic acid can be in the range as described for dip coating.

Optionally, a UV activatable photogroup can be included in the extruded composition including the vinyl pyrrolidone polymer/thermoplastic polymeric material, in the coating bath of polyacrylic acid, or both. UV activatable photogroup may be present on a crosslinking compound, pendent from a polymeric material, or both. If the device with coating is formed using a UV activatable group the extrusion and coating can be followed by a step of UV curing, where the extruded and coated device is moved through a UV irradiation area. A step of UV curing can be performed, for example, to promote covalent bonding via the UV activatable group, in the extruded material, the applied acrylic acid polymer-containing coating, or both.

In the case where the extruded, coated device is in the form of flexible tubing, the method can optionally include an apparatus to collect the tubing, such as an automated rolling apparatus.

In other modes of practice, the coating including acrylic acid polymer can be applied to the extruded material surface after the extruded device has been cooled in a water bath. For example, another method for preparing the coated device includes a step of extruding a composition comprising vinyl pyrrolidone polymer and a thermoplastic using extrusion equipment, a step of cooling the extruded device in a water bath, and then a step of coating the cooled, extruded device with a composition comprising acrylic acid polymer. The coating composition can be applied using an application having a rotating feature, such as described in U.S. Pat. No. 7,192,484 (Chappa et al.)

Optional steps of UV curing in a UV irradiation area and tubing collection, using an automated rolling apparatus, can be performed.

In other modes of practice, one or more of the coating compositions (e.g., first, second) are applied using a coating apparatus as describe in U.S. Publication No. 2013/0337147 (Chappa et al.) which describes a coating method and apparatus having a coating application unit comprising a movement restriction structure; a fluid applicator; an air nozzle; and a rotation mechanism; and an axial motion mechanism, the axial motion mechanism configured to cause movement of at least one of the coating application unit and the rotation mechanism with respect to one another.

Substrates on which the coating can be formed can be partially or entirely fabricated from a metal, ceramic, glass, or the like, or a combination thereof. Substrates can include polymers such as polyurethanes and polyurethane copolymers, polyethylene, polyolefins, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate can be made of a single material, or a combination of materials.

Substrate polymers can also include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

In some embodiments, the substrate includes a polymer selected from the group consisting of polyamide, polyimide, polyether block amide (PEBAX), polyether ether ketone (PEEK), high density polyethylene (HDPE), polyethylene, polyurethane, and polyethylene vinyl acetate.

Metals that can be used as substrates in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

In some embodiments the substrate, or a portion of the substrate, is formed by melt extruding a thermoplastic elastomer with a vinyl pyrrolidone polymer. A "thermoplastic elastomer" (or a "thermoplastic rubber") refers to a rubber-like material that can be processed like thermoplastic materials. Thermoplastic elastomers include copolymers and polymer blends, including those specifically described herein, having elastomeric and thermoplastic properties. Thermoplastic elastomers include styrene-based block copolymers, polyolefin polymers, thermoplastic polyurethanes, thermoplastic copolyesters, and thermoplastic polyamides, such as polyether block amide (PEBAX) polymers.

Melt extrusion can be carried out by combining raw polymeric materials including a thermoplastic elastomer, such as PEBAX, and a vinyl pyrrolidone polymer, such poly(vinyl pyrrolidone) (PVP). In some modes of practice, the extrusion uses a mixture of having an amount of vinyl pyrrolidone polymer that is lower than the amount of the thermoplastic elastomer (e.g., a low PVP/PEBAX ratio). For example, in some embodiments the vinyl pyrrolidone polymer is present in the extrusion composition in an amount of about 45% (wt) or less, about 40% (wt) or less, about 35% (wt) or less, or about 30% (wt) or less; such as in the range of about 5% (wt) to about 45% (wt), or about 10% (wt) to about 40% (wt). In some embodiments the thermoplastic elastomer, such as PEBAX, is present in the extrusion composition in an amount of about 55% (wt) or greater, about 60% (wt) or greater, about 65% (wt) or greater, or about 70% (wt) or greater; such as in the range of about 55% (wt) to about 95% (wt), or about 60% (wt) to about 90% (wt).

Melt extrusion of the polymeric materials can be performed using methods and melt extrusion equipment known in the art. For example, the polymeric starting materials, such as in the form of pellets or granules, can be fed into feeders which provide the pellets/granules into a mixing barrel having one or more heat zone(s). The melt extruder can include a screw for the heating and mixing of prior to extrusion through the die.

In some embodiments, the melt extruded polymeric materials forms most or all of the device material. For example, melt extruded PVP/PEBAX can form a conduit, such as tubing that can be a part of a catheter assembly as described herein or those known in the art. The melt extruded PVP/PEBAX can then be coated with a composition that includes an acrylic acid polymer on the outer surface, inner surface, or both outer and inner surfaces using techniques as described herein.

In other cases, melt extruded PVP/PEBAX can form a portion of the medical device, with the coating that includes the acrylic acid polymer in contact with the PVP/PEBAX portion. For example, the PVP/PEBAX can form a first portion of the device in contact with the coating, and the device can include a second portion, etc., that is a distinct portion of the device made from a different material, or different material combination.

In some modes of construction, the extruded PVP/PEBAX is present as a first portion of the device that is formed by extrusion on another (e.g., second) portion of the device. The second portion of the device can be made from another thermoplastic, or made from a metal. The second portion of the device can be formed into a desired shape or configuration prior to extruding the PVP/PEBAX on the second portion.

In other modes of construction, the PVP/PEBAX can be co-extruded with a different thermoplastic, or different thermoplastic combination, so the PVP/PEBAX forms a first portion of the device, and the different thermoplastic forms a second portion of the device. For example, PVP/PEBAX can be co-extruded with a nylon or PTFE.

In some constructions the PVP/PEBAX is extruded as a thin layer (first portion) on a second portion of the device that substantially thicker than the first portion. For example, the PVP/PEBAX is extruded as a thin layer on the inner surface, outer surface, or both inner and outer surface of the second portion of the device which is a tube made from a different thermoplastic, such as nylon or PTFE, or metal. The melt extruded PVP/PEBAX forming the thin layer can then be coated with a composition that includes the acrylic acid polymer using techniques as described herein.

Optionally, a UV activatable photogroup can be included in the extruded PVP/PEBAX device, extruded PVP/PEBAX layer, acrylic acid polymer-containing coating, or combinations thereof. The UV activatable photogroup may be present on a crosslinking compound, pendent from a polymeric material, or both.

The methods and materials of the disclosure can be utilized to coat virtually any medical device for which it is desired to provide a hydrophilic and lubricious coating on a surface. In particular, the coatings are particularly useful for medical articles that can be inserted into and moved within the body.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff; sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products, vena cava filters, and embolic protection filters and devices and electrophysiology mapping and ablation catheters.

In some embodiments coatings of the present disclosure can be used on exemplary medical devices such as braided catheters. In yet other embodiments the coatings can be used advantageously on braided catheters (e.g. PEBAX®).

Figure 4:
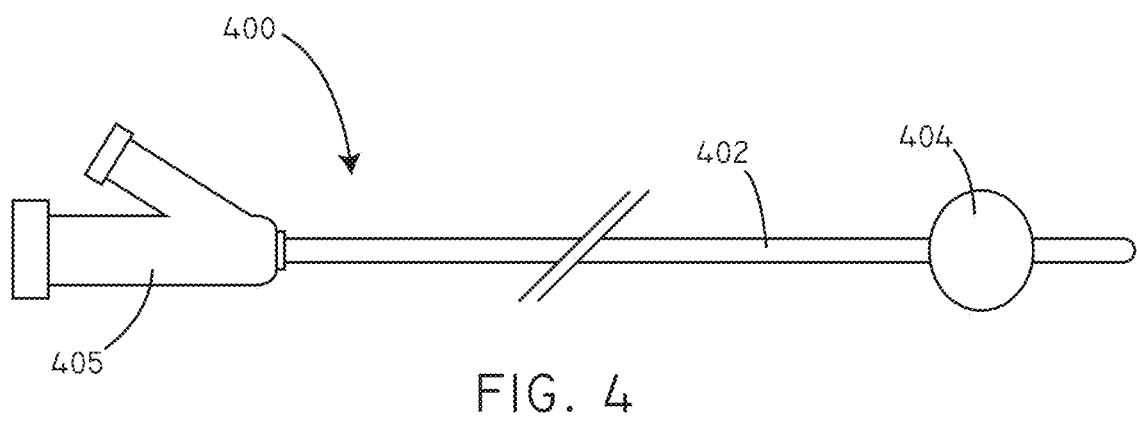
FIG. 4 is a schematic view of an embodiment of a coated medical device.

FIG. 4 is a schematic view of an exemplary device is shown in accordance with a specific embodiment. The device 400 can be, for example, a catheter, such as an angioplasty balloon catheter. Balloon catheter constructions are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. The device 400 includes a catheter shaft 402 and a manifold end 405. The device 400 also includes an inflatable balloon 404 disposed around the catheter shaft 402. In FIG. 4, the balloon 404 is shown in an inflated configuration. The catheter shaft 402 can include a channel to convey air through the catheter shaft 402 and to or from the balloon 404, so that the balloon 404 can selectively go from a deflated configuration to the inflated configuration and back again. The catheter shaft, and/or the balloon, can have a coating, such as those described herein, disposed thereon.

Aspects may be better understood with reference to the following examples. These examples are intended to be representative of specific embodiments, but are not intended as limiting the overall scope of embodiments herein.

EXAMPLES

The following reagents, coating solutions, and substrates were used for the examples herein:

PA-BBA-AMPS-PEG

N-Acetylated poly[acrylamide$^{93.6\%}$-co-sodium-2-acrylamido-2-methylpropanesulfonate$^{4.9\%}$-co-N-(3-(4-benzoylbenzamido)propyl)methacrylamide$^{0.9\%}$]-co-methoxy poly(ethylene glycol)1000 monomethacrylate$^{0.6\%}$ (percentages are mole percents) was obtained (PA-BBA-AMPS-PEG). This reagent can be prepared as described in U.S. Pat. Nos. 4,979,959; 5,263,992; and 5,512,329.

Photo-PVP

Polyvinylpyrrolidone having an average molecular weight of about 1,450 kDa with benzophenone photoreactive groups was prepared according to the methods described in U.S. Pat. No. 5,512,329.

BPP

The cross-linking agent sodium bis(4-benzoylphenyl) phosphate was prepared according to the methods described in U.S. Publ. Pat. App. No. 2011/0245367.

PAA Acid Form

Poly(acrylic acid) having an average molecular weight of 450 kDa was purchased from Sigma-Aldrich.

PAA Partial Salt Form

A partially salted poly(acrylic acid) was synthesized by polymerizing acrylic acid in deionized water using free radical initiation. First, acrylic acid (0.8 M) was dissolved in deionized water with stirring in a glass reaction vessel. To this solution, 6 N sodium hydroxide was slowing added to partially salt the acid functionality. Next, the initiator ammonium persulfate was added to the reaction vessel with stirring. The polymerization solution was then degassed with nitrogen and placed at 55° C. for sixteen hours with stirring. After polymerization, the polymer was dialyzed versus continuous flow deionized water using 12-14 K dialysis tubing. Lastly, the polymer was isolated via lyophilization.

Coating Solution A

A coating solution was prepared by mixing together Photo-PVP at 18 g/L; and BPP at 1 g/L in a solvent of 75% isopropyl alcohol and 25% water.

Coating Solution B

A coating solution was prepared by mixing together PAA (acid form) at 10.5 g/L; PA-BBA-AMPS-PEG at 10.5 g/L; BPP at 0.1 g/L in a solvent of 15% isopropyl alcohol and 85% water.

Coating Solution C

A coating solution was prepared by mixing together PAA (partial salt form) at 10.5 g/L; PA-BBA-AMPS-PEG at 10.5 g/L; BPP at 0.1 g/L in a solvent of 15% isopropyl alcohol and 85% water.

Coating Solution D

A coating solution was prepared by dissolving PAA (partial salt form) at 20 g/L in a solvent of 15% isopropyl alcohol and 85% water.

Test Substrate

The test substrate was Pebax rods (72D) obtained from Medicine Lake Extrusions, Inc., Plymouth, Minn.

Coating Pebax Substrate

Coatings were applied to Pebax catheter material (72D Pebax rods). Specifically, coating solution A was applied as a base coat to the substrate using a dip coat method. The substrate was immersed in the base coat coating solution with a dwell time of 5 seconds. The substrate was then extracted from the solution at a speed of 1.5 cm/s. The first polymeric layer was then air dried for at least 10 minutes. The first polymeric layer was then UV cured. Specifically, the coated substrate was rotated in front of a Dymax 2000-EC series UV flood lamp with a 400 Watt metal halide bulb for 30 seconds, approximately 20 cm from the light source. Next, a layer of coating solution B, C, or D was applied to the base coat layer, by dip coating at a speed of 0.3 cm/s to form the second polymeric layer. The second polymeric layer was then air dried and UV cured using the same conditions as for the base layer. Coated rods were then subjected to various base treatments and sterilized by ethylene oxide (EtO) gas.

Friction (Lubricity) and Durability Testing

The coated substrates of the examples were evaluated for lubricity/durability by friction measurements using a Vertical Pinch Method, as described in U.S. Publ. Appl. No. 2003/0165613, with the following modifications. The coated substrate samples were hydrated in phosphate-buffered saline (PBS, pH 7.4) for >=1 minute and then inserted into the end of a rod holder, which was placed between the two jaws of a pinch tester and immersed in a cylinder of PBS. The jaws of the pinch tester were closed as the sample was pulled in a vertical direction for 10 cm at a travel rate of 1 cm/sec and opened when the coated sample was returned to the original position. A 750 g force was applied as the coated substrates were pulled up through the pinched jaws. The pull force exerted on the substrate was then measured (grams). Pull force (g) is equal to the coefficient of friction (COF) multiplied by pinch force. The apparatus used for the vertical pinch test method is described in U.S. Pat. No. 7,348,055, the content of which is herein incorporated by reference.

Example 1: Various Base Treatments of Pebax Rods Coated with Coating Solution C

Pebax rods, top coated with coating solution C, were treated with either sodium hydroxide or sodium bicarbonate. The sodium hydroxide treatment consisted of soaking rods in 1 N NaOH for 30 seconds and then immediately rinsing the rods with PBS. The rods were briefly rinsed with deionized water and air dried.

For the sodium bicarbonate treatment, a solution of 0.1 M NaHCO$_3$ was prepared in deionized water. The resulting pH was 8.12. Coated Pebax rods were immersed in the sodium bicarbonate solution for 30 seconds and then removed. The rods were briefly rinsed in deionized water and then air dried.

Figure 5:
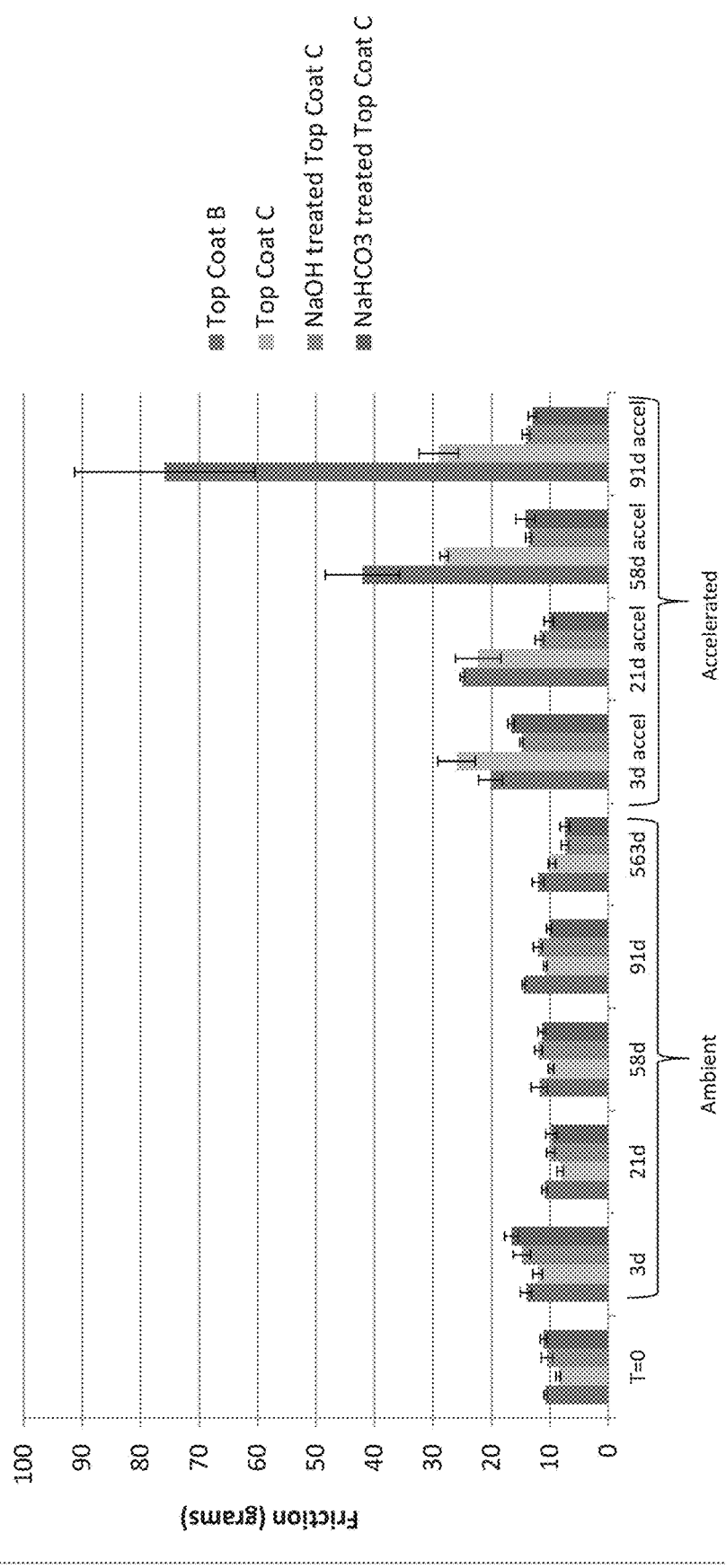
FIG. 5 is a graph showing the average measured frictional force in a vertical pinch test over a number of testing cycles.

All rods were sterilized by ethylene oxide (EtO) gas at Steris Isomedix Services (Minneapolis, Minn.). An accelerated aging study was initiated to determine the lubricity stability of the coatings. Sets of coated rods were subjected to either ambient conditions (benchtop) or accelerated aging conditions (55° C., 50% RH) for up to 91 days. Under the accelerated aged condition, 91 days is equivalent to approximately two years real time. At designated time points, rods were tested for lubricity by friction measurements using a vertical pinch method. The results are shown in FIG. 5.

The lubricity of all rods stored under ambient conditions remained stable for the duration of the study. Under the accelerated aged condition, the lubricity of the PAA containing coating with salt groups was less affected by EtO sterilization than the acid form. Base treatment with either NaOH or NaHCO$_3$ was effective to maintain strong lubricity performance of the coatings under accelerated aged conditions.

Example 2: Sodium Bicarbonate Treatment of Pebax Rods Coated with Coating Solution D Sodium bicarbonate treatments were examined further by comparing a quick sodium bicarbonate treatment method to the standard treatment as described in Example 1. In this case, rods were top coated with coating solution D. The 'quick' treatment consisted of immersing coated rods into sodium bicarbonate and then immediately removing them from the solution (no dwell time). The rods were then air dried. There was no rinse step in between removing the rods from the sodium bicarbonate solution and the drying step.

Figure 6:
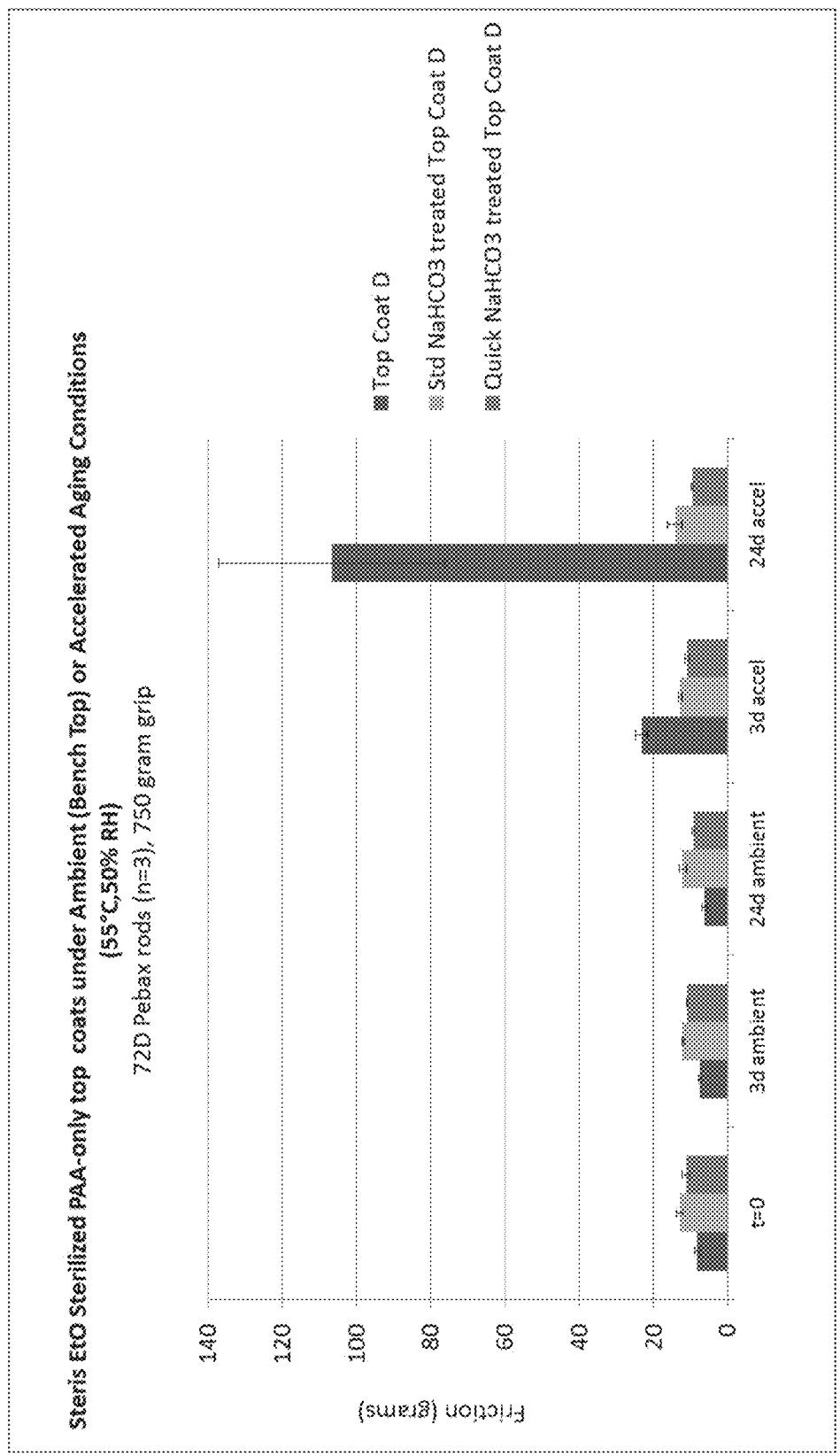
FIG. 6 is a graph showing the average measured frictional force in a vertical pinch test over a number of testing cycles.

All rods were sterilized by EtO gas at Sterigenics, Inc. (Willowbrook, Ill.). An accelerated aging study was initiated to determine the lubricity stability of the coatings. Sets of coated rods were subjected to either ambient conditions (benchtop) or accelerated aging (55° C., 50% RH) for up to 24 days. At designated time points, rods were tested for lubricity by friction measurements using a vertical pinch method. The results are shown in FIG. 6.

The non-treated PAA control rods lost lubricity under the accelerated condition. The quick sodium bicarbonate treatment was just as effective at stabilizing the lubricity performance of the rods and the standard treatment method.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A medical device comprising
a base coat layer disposed on a substrate, wherein the base coat layer comprises a vinyl pyrrolidone polymer;
a polymeric layer disposed on the base coat layer, the polymeric layer comprising an acrylic acid polymer comprising carboxylic acid groups on an outer surface thereof;
wherein a portion of the carboxylic acid groups are in salt form, the salt form portion comprising from 10 to 99 percent of the carboxylic acid groups by number;
wherein the carboxylic acid groups having a pKa from 3.5 to about 5; and
wherein the carboxylic acid groups are disposed throughout a thickness of the polymeric layer.

2. The medical device of claim 1, the carboxylic acid groups having a pKa from 4.2 to 4.5.

3. The medical device of claim 1, the salt form of the carboxylic acid groups comprising a salt selected from the group consisting of sodium, potassium, lithium, calcium, aluminum, zinc, magnesium and ammonium salts.

4. The medical device of claim 1, the salt form portion comprising from 40 to 99 percent of the carboxylic acid groups by number.

5. The medical device of claim 1, the salt form portion comprising from 60 to 90 percent of the carboxylic acid groups by number.

6. The medical device of claim 1, further comprising trace amounts of carbonate disposed on the polymeric layer surface.

7. The medical device of claim 1, the polymeric layer comprising poly(acrylic acid).

8. The medical device of claim 1, further comprising a base coat layer disposed over the substrate and under the polymeric layer.

9. The medical device of claim 8, the base coat layer comprising photoreactive groups.

10. A method of making a medical device comprising:
obtaining a medical device comprising a polymeric layer disposed over on a substrate, the polymeric layer comprising an exterior surface with carboxylic acid groups disposed on the exterior surface; and
applying a solution to the exterior surface, the solution comprising a carbonate or bicarbonate salt, wherein the carbonate or bicarbonate in the solution reacts with the carboxylic acid groups to form salt groups;
the salt groups comprising from 10 to 99 percent of the carboxylic acid groups by number;
wherein the carboxylic acid groups having a pKa from 3.5 to about 5; and
wherein the carboxylic acid groups are disposed throughout a thickness of the polymeric layer.

11. The method of claim 10, comprising a salt selected from the group consisting of sodium, potassium, lithium, calcium, aluminum, zinc, magnesium and ammonium salts.

12. The method of claim 10, the salt groups comprising from 40 to 99 percent of the carboxylic acid groups by number.

13. The method of claim 10, the salt groups comprising from 60 to 90 percent of the carboxylic acid groups by number.

14. The method of claim 10, wherein the exterior surface comprises trace amounts of carbonate disposed on the polymeric layer surface.

15. The method of claim 10, the polymeric layer comprising poly(acrylic acid).

16. The method of claim 10, further comprising applying a base coat layer disposed over the substrate and under the polymeric layer.

17. The method of claim 10, the base coat layer comprising photoreactive groups.

18. The method of claim 10, the base coat layer comprising a vinyl pyrrolidone polymer.

* * * * *